(12) United States Patent
Shin et al.

(10) Patent No.: US 6,383,521 B1
(45) Date of Patent: May 7, 2002

(54) WONDONIN A AND PROCESS FOR PREPARING THE SAME

(75) Inventors: Jong-Heon Shin, Ansan-shi; Ki-Woong Cho, Seoul; Young-Wan Seo, Ansan-shi; Jung-Rae Rho, Seoul; Hyi-Seung Lee, Seoul; Ho-Jeong Kwon, Seoul, all of (KR)

(73) Assignee: Korea Ocean Research and Development, Kyonggi-do (KR)

( * ) Notice: Subject to any disclaimer, the term of this patent is extended or adjusted under 35 U.S.C. 154(b) by 0 days.

(21) Appl. No.: 09/839,393

(22) Filed: Apr. 20, 2001

(30) Foreign Application Priority Data

Apr. 20, 2000 (KR) .......................... 00-0020907

(51) Int. Cl.[7] .............................. C07D 307/00
(52) U.S. Cl. ................... 424/520; 548/100; 549/430; 549/432; 549/448
(58) Field of Search ................... 424/520; 548/100; 549/430, 432, 448

(56) References Cited

U.S. PATENT DOCUMENTS 5,328,929 A * 7/1994 Pettit et al.
5,464,835 A * 11/1995 McConnell et al.
5,591,740 A * 1/1997 Chipman et al.
5,834,609 A * 11/1998 Horne et al.

OTHER PUBLICATIONS

Shin et al., Wondonins A and B, new bis(dihydroxystyryl)imidazoles from a two–sponge association, *Tetrahedron Letters* 42: 1965–1968 (2001).

* cited by examiner

*Primary Examiner*—Leon B. Lankford, Jr.

(57) ABSTRACT

The present invention provides Wondonin A of general formula (I), which is extracted from a two-sponge association of *phylum Porifera* (sponge) and has antiangiogenic activity, and a process for preparing the same. Wondonin A has no cytotoxicity, but has an inhibitory activity against angiogenesis which is one of the crucial mechanisms of cancer cell metastasis, thus, it can be applied not only as an anticancer drug but also as a therapeutic agent of angiogenesis-associated diseases such as cardiac ischemia, rheumatoid arthritis, and diabetes mellitus.

(I)

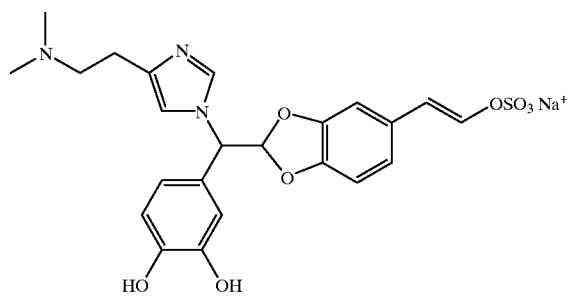

5 Claims, No Drawings

WONDONIN A AND PROCESS FOR PREPARING THE SAME

BACKGROUND OF THE INVENTION

1. Field of the Invention

The present invention relates to Wondonin A and a process for preparing the same, more specifically, to Wondonin A which is extracted from a two-sponge association of phylum Porifera (sponge) and has antiangiogenic activity, and a process for preparing the same.

2. Background of the Invention

In general, malignant tumors contain a lot of hypoxic cells due to an inadequate vasculature (see: Moulder and Rockwell, Cancer Metastasis Rev., 5:313–341, 1987; Vaupel et al., Cancer Res., 49:6449–6465, 1989) or a change in a supply of red blood cells in intratumoral microvessels (see: Kimura et al., Cancer Res., 56:5522–5528, 1996). Although these hypoxic tumor cells may be reoxygenized by reopening of temporally closed or clogged microvessels not to inhibit tumor cell growth (see: Brown, J. M., Br. J. Radiol., 52:650–656, 1979) or reoxygenized by inactivation of tumor cells by fractionated radiation therapy (see: Kallman, R. F., Radiology, 105:135–142, 1972) by which some of them may be converted into normoxic cells, it has been known that hypoxic cells are generally more resistant to radiation therapy or conventional chemotherapy (see: Teicher et. al., Cancer Res., 41:73–81, 1981; Gatenby et al., Int. J. Radiat. Oncol. Biol. Phys., 14:831–838, 1988; Teicher et. al., Cancer Metastasis Rev., 13:139–168, 1994).

Although the adaptation mechanism of tumor cells to a low oxygen tension has not been understood clearly, hypoxia has been known to affect the pattern of gene expression in tumor cells (see: Brown and Giaccia, Int. J. Radiat. Biol., 65:95–102, 1994) and it has been reported that stress reaction of normoxic cells is induced by low-oxygen environment and, in consequence, synthesis of stress proteins is induced in vivo and in vitro (see: Guttman et al., Cell, 22:229–307, 1980; Heacock and Sutherland, Br. J. Cancer, 62:217–225, 1990; Iwaki et al., Circulation, 87:2023–2032, 1993). For example, Baek et al. demonstrated that the synthesis of heat shock proteins such as hsp70 and hsp25 is upregulated in mouse radiation-induced fibrosarcoma (RIF) cells by hypoxia, and hypoxic tumor cells with increased level of heat shock proteins are more resistant to hypoxia than normoxic cells (see: Baek et al., J. Biochem. & Mol. Biol., 32:112–118, 1999).

It has been demonstrated that growth factors such as VEGF (vascular endothelial cell growth factor) (see: Stein et al., Mol. Cell. Biol., 15:5363–5368, 1995), EPO (erythropoietin) (see: Wang and Semenza, Blood, 82:3610–3615, 1993) and TGF β-1 (transforming growth factor β-1) (see: Brown et al., EXS., 79:233–269, 1997) required for angiogenesis which is an essential process for progression and metastasis of hypoxic tumor cells described above can be upregulated by hypoxia. Hence, cooperative induction of stress protein and angiogenesis factor genes are understood to render tumor cells adaptable to low oxygen stress, helping progression of tumor cells toward more malignant phenotype.

In order to overcome problems caused by hypoxic tumor cells, three methods are conventionally employed in the art: (i) oxygenation of tumor cells; (ii) attenuation of hypoxic cells with radiation or chemotherapy; and (iii) hypoxic cell death by a hypoxic cell cytotoxin (see: Brown and Kong, J. Intl. Cancer Inst., 83:178–185, 1991). However, hypoxic tumor cells are resistant to both radiation and chemotherapy, thus, researchers on development of methods which can increase curative efficiency for tumor cells are being undertaken, and yet, side effects of the substances which inhibit synthesis of proteins required for angiogenesis are so severe that there has been no progress of the research.

Under the circumstances, there are strong reasons for exploring and developing natural compounds which has antiangiogenic activity without side effects.

SUMMARY OF THE INVENTION

The present inventors have made an effort to develop a natural product which has antiangiogenic activity without side effects, and discovered that Wondonin A, a novel compound extracted from phylum Porifera, can exert inhibitory activity against angiogenesis without cytotoxicity.

A primary object of the present invention is, therefore, to provide Wondonin A extracted from phylum Porifera.

The other object of the invention is to provide a process for preparing Wondonin A.

DETAILED DESCRIPTION OF THE INVENTION

Wondonin A of the present invention is represented as general formula (I) below:

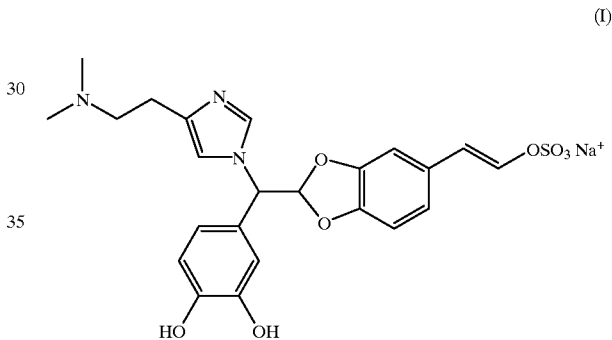

(I)

Wondonin A, which is an aromatic alkaloid, has a combined carbon backbone of 3,4-dihydroxystyrylsulfate, 3,4-dihydroxystyrene and N,N-dimethylethenylimidazole, where two hydroxyl groups of styrylsulfate bind each other to form a pentagonal hemiketal.

Wondonin A of the present invention is prepared by a process comprising the steps of: extracting a two-sponge association of phylum Porifera, *Poecillastra wondoensis* grown on Jaspis sp. with an organic solvent and drying the extract under a reduced pressure to give an extract; fractionating the extract by polarity with an organic solvent and drying polar fraction thus obtained under a reduced pressure to yield a polar extract; and, isolating and purifying the polar extract by the aid of chromatography. Organic solvents to be used for extraction of Wondonin A includes methanol, ethanol, chloroform, acetone, dichloromethane, and mixture thereofs, while the organic solvents for fractionation of extract include a mixture of water and dichloromethane and a mixture of water and buthanol, and combination thereofs. On the other hand, the chromatography includes reversed-phased vacuum flash chromatography, Diaion HP-20 adsorption chromatography, chromatography employing $C_{18}$ reversed-phase semi-preparative HPLC column and combination thereofs.

Wondonin A of the invention possesses antiangiogenic activity and inhibits tissue invasion ability of endothelial cells, while showing no direct toxicity to endothelial cells. That is, Wondonin A has no cytotoxicity, but has an inhibitory activity against angiogenesis which is one of the crucial mechanisms of cancer cell metastasis, thus, it can be applied not only as an anticancer drug but also as a therapeutic agent of angiogenesis-associated diseases such as cardiac ischemia, rheumatoid arthritis, and diabetes mellitus.

The present invention is further illustrated in the following examples, which should not be taken to limit the scope of the invention.

EXAMPLE 1

Preparation of Wondonin A

After cutting 12 kg of two-sponge association of phylum Porifera, *Poecillastra wondoensis* grown on Jaspis sp. to a size of 3 cm, 15 L of methanol was added, left to stand for 48 hours and filtered, and repeated the said steps 3 times. And then, 15 L of dichloromethane was added to the filtered solid, left to stand for 48 hours and filtered, and repeated the said steps 2 times. Then, methanol fitrates and dichloromethane filtrates were mixed and solvents were removed under a reduced pressure to yield 375.4 g of dried extract. After mixing the said extract with water and dichloromethane (1 L each), aqueous layer was separated therefrom and dried under a reduced pressure to yield 357.9 g of residue. And again, water and buthanol (1 L each) were mixed with the said residue, aqueous layer was separated and then dried under a reduced pressure to yield 12.9 g of polar organic material. The polar organic material thus obtained was fractionated by employing reversed-phase vacuum flash chromatography. The column used was a glass filter column 100×95 mm (inner diameter×length), the stationary phase was $C_{18}$ semi-preparative silica for TLC, eluent was 50–100% (v/v) methanol in water, and washing solution was acetone and dicholoromethane. Each fraction was identified with $^1$H-NMR spectrophotometry to choose 4.6 g of active fraction, which was further fractionated by employing Diaion HP-20 adsorption chromatography. The column used was glass filter column (50×100 mm, inner diameter×length), the stationary phase was Diaion HP-20, and eluents used were water, 50% (v/v) methanol in water, 50% (v/v) acetone in water, 100% (v/v) methanol, and 100% (v/v) acetone, consecutively. Among the eluates, 50% (v/v) acetone in water fraction was dried under a reduced pressure to yield 0.45 g of residue, which was dissolved in 60% (v/v) methanol, filtered, and then fractionated by employing reversed-phase vacuum flash chromatography. The column used was $C_{18}$ reversed-phase semi-preparative HPLC column (YMC-ODS column, particle diameter 5 μm, 10×250 mm (inner diameter×length), eluent: 60% (v/v) methanol, elution rate: 2 ml/min, refractive meter) and viscous eluate at 28 min was collected. Finally, the viscous liquid thus obtained was dissolved in 65% (v/v) methanol in water, purified by employing the same $C_{18}$ reversed-phase semi-preparative HPLC column (eluent: 65% (v/v) methanol in water, elution rate: 2 ml/min, refractive meter), and fraction at 11 min was collected to yield 16 mg of viscous semi-solid Wondonin A.

EXAMPLE 2

Structure Identification of Wondonin A

The chemical structure of Wondonin A was identified on the basis of spectral data such as NMR, UV and IR and physicochemical data, which revealed that Wondonin A is an alkaloid with a molecular weight of 525 Da represented by molecular formula $C_{23}H_{24}N_3O_8SNa$. Wondonin A is a stable pale-yellow semi-solid at room temperature and highly soluble in polar organic solvents such as methanol and dimethylsulfoxide. The spectrophotomeric data of Wondonin A are as follows:

Infrared band (KBr): 3400, 1650, 1495, 1245, 1035 $cm^{-1}$

Ultraviolet band (MeOH): 210 (log $\epsilon$4.16), 264 (log $\epsilon$3.94) nm $^1$H NMR (500 MHz): δ 2.35 (s, 6H), 2.54 (m, 1H), 2.62 (m, 1H), 2.82 (t, 2H), 5.58 (d, 1H), 6.11 (d, 1H), 6.60 (d, 1H), 6.65 (dd, 1H), 6.79 (d, 1H), 6.81 (d, 1H), 6.90 (dd, 1H), 6.92 (s, 1H), 7.00 (d, 1H), 7.14 (d, 1H), 7.61 (s, 1H)

$^{13}$C NMR (125 MHz): 24.9 t, 44.2 q, 59.3 t, 64.3 d, 105.9 d, 109.6 d, 110.9 d, 115.4 d, 116.6 d, 116.9 d, 118.4 d, 121.3 d, 121.5 d, 126.5 s, 130.3 s, 138.1 s, 139.4 d, 140.0 d, 146.9 s, 147.3 s, 147.5 s, 149.0 s

EXAMPLE 3

Inhibitory Effect of Wondonin A on Tissue Invasion Activity of Endothelial Cells Powdered medium 199 (M 199, Sigma Chemical Co., U.S.A.) and 2.2 g (per liter) of sodium bicarbonate was dissolved in double distilled water, pH of the medium was adjusted to 7.2 with HCl, and followed by sterile filtration on a 2 μm Millipore filter. Then, a medium was finally prepared by supplementing, just before use, with 20% (w/v) FBS (fetal bovine serum ), 1% (w/v) Penicillin-Streptomycin (P-S), 3 ng/ml bFGF (basic fibroblast growth factor, a growth factor for angiogenesis) and 100 μg/ml heparin. Human umbilical vascular endothelial cells ("HUVEC") purchased from ATCC (American Type Culture Collection) were seeded to 6 ml of the medium thus prepared in a T25 flask (25 $cm^2$) and grown to form a monolayer in an incubator at 37° C. under an environment of 5% (v/v) $CO_2$ and saturated humidity, and then subcultured in a medium containing 0.05% (w/v) Trypsin-EDTA.

For invasion assay, lower surface of the polycarbonate filter (pore size: 8 μm) equipped in an insert chamber was coated with 5 μg of Type IV collagen and upper surface of the filter was coated with 25 μg of Matrigel (Collaborative Research, Inc., Waltham, Mass., U.S.A.). For a control group, the coated filter was placed in a main chamber (24 well plate) containing 600 μl of medium supplemented with bFGF (a growth factor for angiogenesis), 5×10$^4$ cells/well of cultured cells, 6 μl of BSA and 6 ul of medium free of Wondonin A. For a test group, the filter was treated in an analogous manner as in a control group except for adding 6 ul of medium containing 10 μg/ml of Wondonin A. After incubating above test and control plates at 37° C. for 18 hours, polycarbonate filters were taken out from the insert chamber and fixed. After staining of the fixed cells with haematoxillin and eosin, Matrigel was detached from the filter and HUVEC cells which have passed through the filter were counted. In the test group, 66% reduction in a cell number passed through the filter was observed compared to the control group. Accordingly, it was clearly demonstrated that Wondonin A efficiently blocks cancer cell metastasis, since it inhibits tissue invasion activity of endothelial cells.

EXAMPLE 4

Effect of Wondonin A on Viability of Vascular Endothelial Cells

Vascular endothelial cells grown on Example 3 were placed onto a 24-well plate with 5×10$^4$ cells/well starting cell number in 1 ml (per well) of the same medium as in Example 3 except for containing 10% (v/v) FBS, and incubated at 37° C. under an environment of 5% (v/v) $CO_2$ for 24 hours to the level of 80% cell confluency. Then, cells were rinsed with 1 ml of PBS and 1 ml of the same medium without FBS was added and then Wondonin A was added to reach the concentrations of 0, 10 and 10 μg/ml, respectively. After 48 hour incubation, medium was removed and cells were harvested by trypsinization. Cells were stained in a medium containing 0.4% (w/v) Trypan Blue at room temperature and then counted with haemacytometer. The cell viability was assessed based on total cell number and stained cell number (see: Table 1).

TABLE 1

Cytotoxic effect of Wondonin A on cell viability

| Concentration of Wondonin A (μg/ml) | 0 | 1 | 10 |
|---|---|---|---|
| Viability (%) | 100 | 98 | 97 |

As shown in Table 1 above, Wondonin A was found to exert no effect on the viability of vascular endothelial cells. From the results of Examples 3 and 4, it was clearly demonstrated that Wondonin A can be applied as an active ingredient of anticancer agent in a safe manner, since it does not affect on the viability of normal cells while inhibiting the metastasis of tumor cells.

EXAMPLE 5

Inhibitory Effect of Wondonin A on Angiogenesis

To investigate whether Wondonin A also inhibits neovascularization in vivo, chick embryo chorioallantoic membrane assay was performed: that is, after incubation of freshly fertilized egg for 3 days, 2 ml of egg albumin was removed to detach eggs yolk from chorioallantoic membrane. On day 3.5, a part of egg shell was cracked gently, and on day 4.5, a cover slip containing Wondonin A (prepared by drying 21 μl of 10 μg/ηl Wondonin A in methanol on a cover slip) or a control cover slip (prepared by drying 2 μl of methanol on a cover slip) was placed on the chorioallantoic membrane (CAM) through the crack and then the crack was sealed. After incubation for 2 days, 10% fat emulsion was injected to CAM, which was examined under a microscope. The embryos with a clear avascular zone (inhibition of angiogenesis) were counted and inhibitory effect of Wondonin A on angiogenesis was evaluated by calculating the ratio of the number of embryo with avascular zone to the total number of embryo tested (see: Table 2).

TABLE 2

Inhibitory effect of Wondonin A on angiogenesis

| | Inhibition of angiogenesis (%) |
|---|---|
| Control group | 21 |
| Test group | 89 |

As shown in Table 2, Wondonin A was found to inhibit angiogenesis, assuring that Wondonin A can block the metastasis of cancer cells.

As clearly illustrated and demonstrated as above, the present invention provides Wondonin A, which is extracted from a two-sponge association of *phylum Porifera* and has antiangiogenic activity, and a process for preparing the same. Wondonin A of the invention has no cytotoxicity, but has an inhibitory activity against angiogenesis which is one of the crucial mechanisms of cancer cell metastasis, thus, it can be used not only as an anticancer drug but also as a therapeutic agent of angiogenesis-associated diseases such as cardiac ischemia, rheumatoid arthritis, and diabetes mellitus.

What is claimed is:
1. Wondonin A represented as the following general formula (I):

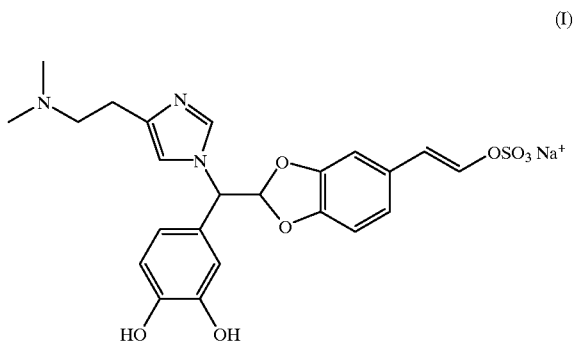

(I)

2. A process for preparing Wondonin A which comprises the steps of:

(i) extracting a two-sponge association of *phylum Porifera, Poecillastra wondoensis* grown on Jaspis sp. with an organic solvent and drying the extract under a reduced pressure to give an extract;

(ii) fractionating the extract by polarity with an organic solvent and drying polar fraction thus obtained under a reduced pressure to yield a polar extract; and, (iii) isolating and purifying the polar extract by the aid of chromatography.

3. The process for preparing Wondonin A of claim 2 wherein the organic solvent used for extraction is selected from the group consisting of methanol, ethanol, chloroform, acetone, dichloromethane and mixture thereofs.

4. The process for preparing Wondonin A of claim 2 wherein the organic solvent used for fractionation is a mixture of water and dichloromethane, a mixture of water and butanol, or combination thereofs.

5. The process for preparing Wondonin A of claim 2 wherein the chromatography is carried out by reversed-phase vacuum flash chromatography, Diaion HP-20 adsorption chromatography, $C_{18}$ reversed-phase semi-preparative HPLC, or combination thereofs.

* * * * *